(12) United States Patent
Hall et al.

(10) Patent No.: US 10,881,544 B1
(45) Date of Patent: Jan. 5, 2021

(54) NECK BRACE

(71) Applicants: UNIVERSITY COLLEGE CARDIFF CONSULTANTS LTD, Cardiff (GB); CARDIFF METROPOLITAN UNIVERSITY, Cardiff (GB)

(72) Inventors: Judith Hall, Cardiff (GB); Stephen Gill, Pontypridd (GB); Gareth Loudon, Newport (GB); Clara Watkins, Cardiff (GB)

(73) Assignees: UNIVERSITY COLLEGE CARDIFF CONSULTANTS LTD, Cardiff (GB); CARDIFF METROPOLITAN UNIVERSITY, Cardiff (GB)

( * ) Notice: Subject to any disclaimer, the term of this patent is extended or adjusted under 35 U.S.C. 154(b) by 182 days.

(21) Appl. No.: 16/336,616

(22) PCT Filed: Sep. 18, 2017

(86) PCT No.: PCT/GB2017/052756
§ 371 (c)(1),
(2) Date: Mar. 26, 2019

(87) PCT Pub. No.: WO2018/055343
PCT Pub. Date: Mar. 29, 2018

(30) Foreign Application Priority Data

Sep. 26, 2016 (GB) .................................. 1616282.8

(51) Int. Cl.
*A61F 5/058* (2006.01)
*A61F 5/055* (2006.01)

(52) U.S. Cl.
CPC .......... *A61F 5/05883* (2013.01); *A61F 5/055* (2013.01)

(58) Field of Classification Search
CPC ........ A61F 5/05883; A61F 5/055; A61F 5/05; A61F 2007/0009; A61F 2007/0011; A61F 13/12; A61F 13/128; A61F 2002/3625; A61F 2002/4029
See application file for complete search history.

(56) References Cited

U.S. PATENT DOCUMENTS 4,209,011 A 6/1980 Peck
4,401,111 A 8/1983 Blackstone
(Continued)

FOREIGN PATENT DOCUMENTS

DE 202015006564 U1 2/2016
EP 0655232 A1 5/1995
ZA 8002624 B 4/1981

OTHER PUBLICATIONS

Search Report from UK Intellectual Property Office dated Feb. 21, 2017.
(Continued)

*Primary Examiner* — Tarla R Patel
(74) *Attorney, Agent, or Firm* — King & Schickli, PLLC

(57) ABSTRACT

The invention concerns a brace, ideally disposable, formed from a blank and, particularly but not exclusively, a neck or limb brace wherein the brace is contoured to fit about a wearer and comprises at least one, or a series of, crease line(s) that mirror(s) the contour of at least one edge of said brace and spaced from same by a selected amount whereby said edge can be folded or torn along at least one selected crease line to fit a wearer.

26 Claims, 3 Drawing Sheets

(56) References Cited

U.S. PATENT DOCUMENTS

| | | | | |
|---|---|---|---|---|
| 5,058,572 A | * | 10/1991 | Schmid | ............ A61F 5/055 602/18 |
| 5,195,944 A | | 3/1993 | Schlogel | |
| 5,305,754 A | | 4/1994 | Honeywell et al. | |
| 5,788,658 A | * | 8/1998 | Islava | ............ A61F 5/055 602/18 |
| 2011/0066094 A1 | | 3/2011 | Thorgilsdottir | |

OTHER PUBLICATIONS

International Search Report and Written Opinion for PCT/GB2017/052756.
DE 202015006564—English machine translation.
EP 0655232—English machine translation.

\* cited by examiner

NECK BRACE

TECHNICAL FIELD

The invention concerns a neck brace, ideally but not exclusively disposable, formed from a blank and wherein the brace is contoured to fit about a wearer and comprises at least one, or a series of, crease line(s) that mirror(s) the contour of at least one edge of said brace and spaced from same by a selected amount whereby said edge can be folded or torn along at least one selected crease line to fit a wearer.

BACKGROUND

Medical braces can be essential items of equipment during instances of medical emergencies, for example, following a road traffic accident or a natural disaster or during times of conflict. In these instances, if assisting personal can secure a body part before transporting an injured person to a medical facility the outcome for the patient can be greatly improved.

However, having access to medical braces and carrying them to sites of use can be problematical. Moreover, different sized individuals need different sized braces and so a range of such braces need to be transported to a site of use and the correct size selected and distributed in what can be hazardous and stressful conditions.

It follows that if it was possible to provide a light-weight but effective brace, whose size could be easily adjusted when used in situ, it would greatly help the emergency services to carry out their task of securing injured individuals prior to transporting them to a hospital for receiving further care.

The invention therefore provides such a brace.

SUMMARY

According to a first aspect, there is provided a neck brace formed from a blank having an axis of symmetry along a mid-line and either side thereof a front and rear section each section comprising:

i) a lower edge, an upper edge, an inner side edge and an outer side edge wherein said lower edge is fashioned to provide a single wave formation and said upper edge is fashioned to provide at least two wave formations and an axis of symmetry of said single wave formation is aligned with an axis of symmetry of said two wave formations;

ii) and further wherein at least one, or a series of, crease line(s) that mirror(s) the contour of at least said lower edge is/are provided and spaced from said lower edge by a selected amount whereby said lower edge can be folded along at least one selected crease line to fit a user;

iii) attached to or associated with said front and rear section, near or at said front and rear side outer edges, is at least one fastening member; and attached to or associated with said upper edge of said front section is a chin supporting member.

In a preferred embodiment said brace is a disposable brace. Not with standing this fact, the brace may be worn for several days if there is not the equipment or opportunity, or even if it is not safe enough, to move the patient or indeed even if there is not suitable medical staff to have the cervical spine 'cleared' i.e. to get a full x-ray of all 7 cervical vertebrae.

In a preferred embodiment said chin supporting member is positioned between adjacent wave formations and, ideally, said chin supporting member is also provided by said blank and comprises a piece thereof which is hingedly attached to said front section for pivoting into position. Alternatively, said chin supporting member is also provided by said blank and comprises a piece thereof which is releasably attached to said front section whereby, in use when attached, it projects forward from said front section.

In a further preferred embodiment said neck brace has between said side inner edges of said front and rear sections at least one adjustment member whereby the said inner edges of said front and rear sections can be brought together by a selected amount. Preferably, said adjustment member comprises a strap and associated restraining member.

In yet a further preferred embodiment said blank is formed from a stiff but flexible material. Preferably, said material is cardboard and, more ideally, a corrugated material such as corrugated cardboard or bubble board. Alternatively, said material is a modified plastic, such as a corrugated plastic material for example Correx™.

Yet more preferably, said blank is formed from at least two materials comprising: a first stiff but flexible material and a second flexible material. Preferably, said materials are overlain and, ideally, said first stiff but flexible material is cut in the same shape as said second flexible material but is smaller whereby, when overlain, the said second flexible material provides a margin about said first flexible material.

In yet a further embodiment of the invention said lower edge is provide with at least one cut or tear. Preferably, said lower edge is provided with a plurality of cuts or tears extending inwards from said edge and, ideally, said cuts or tears are at right angles with respect to said lower edge. Most preferably, said cut(s) or tear(s) is/are provided in the region of a peak of said single wave formation.

In the instance where said two materials are overlain, said cut(s) or tear(s) is/are provided in the said second flexible material.

More preferably still, said crease line(s) mirror(s) the contour of at least said lower edge and also at least one side edge but is/are spaced therefrom by a selected amount. Preferably, said crease line(s) mirror(s) the contour of at least said lower edge and also said front and rear inner and/or outer side edges but is/are spaced therefrom by a selected amount.

In a preferred embodiment three of said crease lines are provided and they are designated, from the lower edge and/or side edge(s) inwards: large medium and small.

In yet another preferred embodiment said crease line(s) is/are also perforated whereby the outer part(s) can be torn away from the main body of the brace.

Preferably, said front section has an opening located in said brace so that, in use, it is aligned with a throat of a wearer.

In a preferred embodiment said fastening member comprises complementary mating members. Preferably, said fastening member comprises a member selected form the group comprising: Velcro® hook and loop material, clasp members, hook/eye members, stud/socket members, magnetic members and adhesive members.

In a further preferred aspect of the invention, optionally, said brace also comprises a further series of crease lines each one defining the outline of an arm or leg brace and so each being of the same shape but representing a different size.

The leg or arm brace is designed to be used above or below a broken bone to reduce movement and create stability and thus reduce bleeding, pain and tissue damage. It can be used in one of two ways:

1. Fracture is a joint: splint bone above and below the joint; or

2. Fracture is not a joint, but a long bone: immobilise joints above and below the fracture.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWING FIGURES

An embodiment of the present invention will now be described by way of example only with reference to the following wherein.

DETAILED DESCRIPTION

Figure 1:
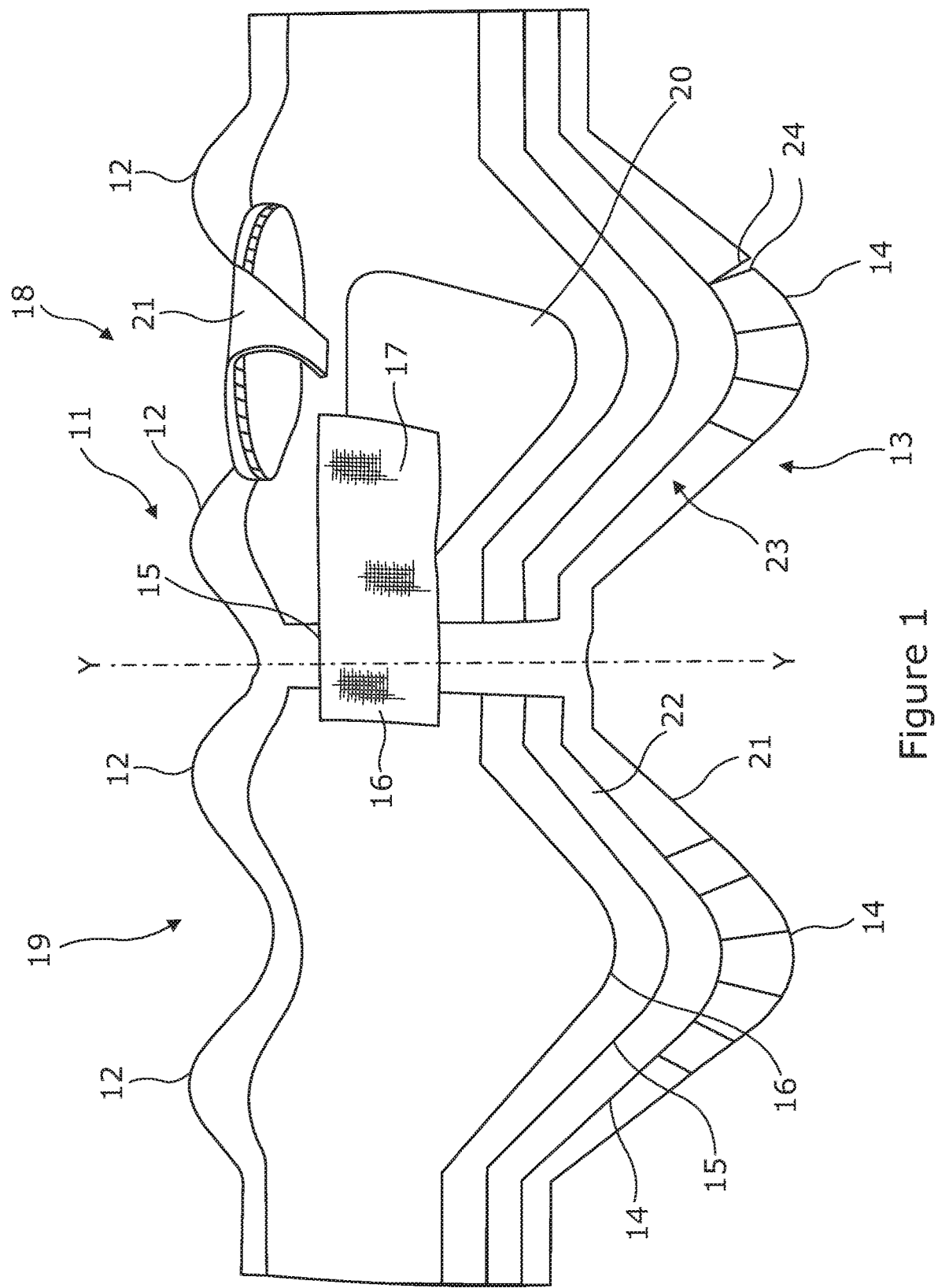
FIG. 1 is a plan view of a neck brace in accordance with the invention.

Referring now to FIG. 1 there is shown a part of a blank that has been cut to form the outline of a neck brace. It has an axis of symmetry along its shortest axis Y, providing to either side thereof a front 18 and rear 19 section. The brace has an upper part terminating in an upper curved edge 11 which defines a number of upper wave forms 12. The brace also has a lower part terminating in a lower curved edge 13 which defines a number of lower wave forms 14. Inward of edges 11 and/or 13 (although only shown with respect to edge 13) are a series of crease lines 14, 15 and 16 which are ideally perforated whereby, in use, the crease lines can be used to fold back parts of the brace to reduce its size or tear away parts of the brace to also reduce its size. Notably, four upper wave forms 12 are provided and two lower wave forms 14 are provided, further the axis of symmetry of wave form 14 is aligned with a mid-point between wave forms 12.

The neck brace also has an adjustment member, in this embodiment, in the form of an adjustable tag 16 and fastener 17 whereby the distance between the front 18 and rear 19 sections of the collar can be adjusted. Front section 18 further comprises a cut-out 20 located in said brace so that, in use, the cut-out sits in front of the throat of a wearer. Cut-out 20 can therefore be used to give access to the trachea for emergency tracheostomy. Above cut-out 20 there is provided a chin support 21. Chin support 21 is either cut from the blank and folded into position using a crease line or it represents a separate piece of material that is attached in conventional fashion to the brace prior to use.

Figure 2:
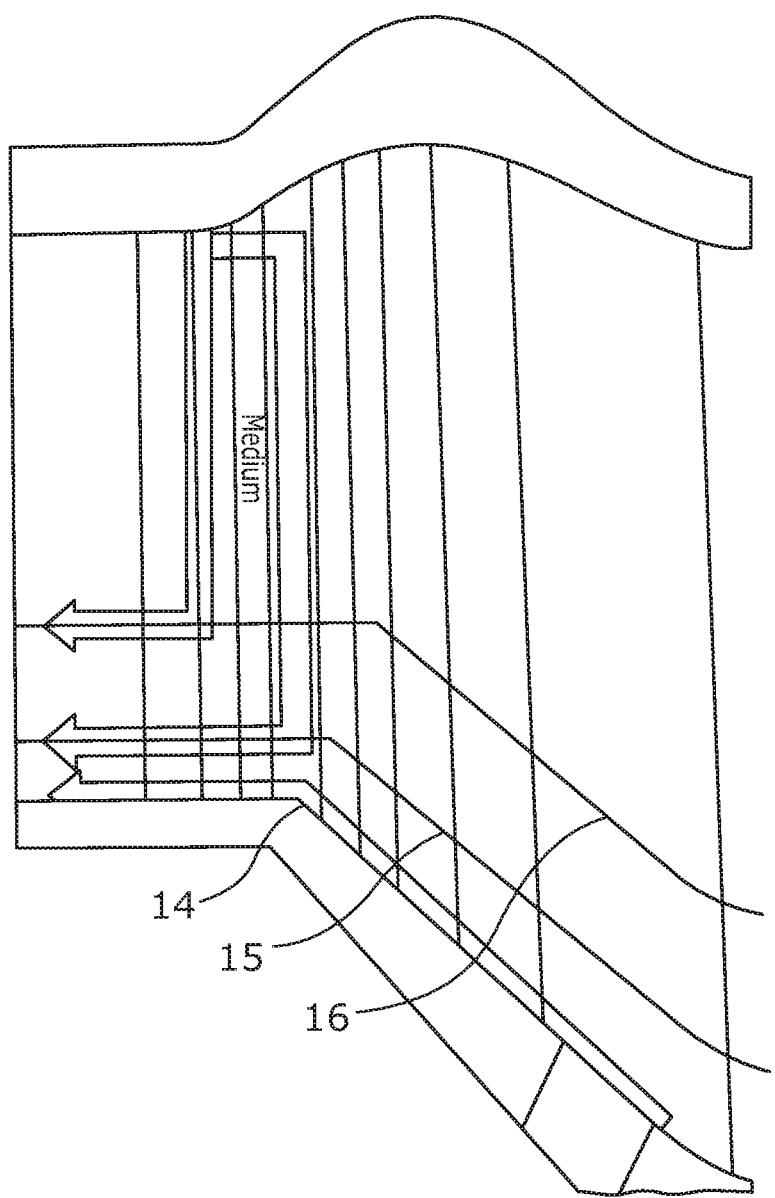
FIG. 2 is a partial plan view of a neck brace in accordance with the invention where the crease or tear lines are colour coded.

Referring to FIG. 2, the neck brace also has a series of markings: crease lines 14, 15 and 16 which are spaced from lower edge 13. Thus in use, one of crease lines 14, 15 and 16 can be selected to fold or reduce the size of the brace to provide a neck brace of a selected size or, by removing extraneous brace material, one of crease lines 14, 15 or 16 can be selected to tear and so reduce the size of the brace to provide a neck brace of a selected size.

The brace is made from a stiff but flexible material so that prior to use it can be folded into a transportable size.

Typically the brace is made from two piece of overlain material: a relatively stiff material and a relatively flexible material. Ideal materials include paper, cardboard, plastics, foam, corrugated materials etc.

The relatively flexible material is cut into the same shape as the relatively stiff material but of a larger size so that when the two materials are overlain the relatively flexible material forms an outer margin. This is illustrated in FIG. 1 where the relatively flexible material is shown as 21 and the relatively stiff material is shown as corrugated card 22. The margin 23 is provided with one or more cuts 24 to facilitate the folding of same.

Figure 3:
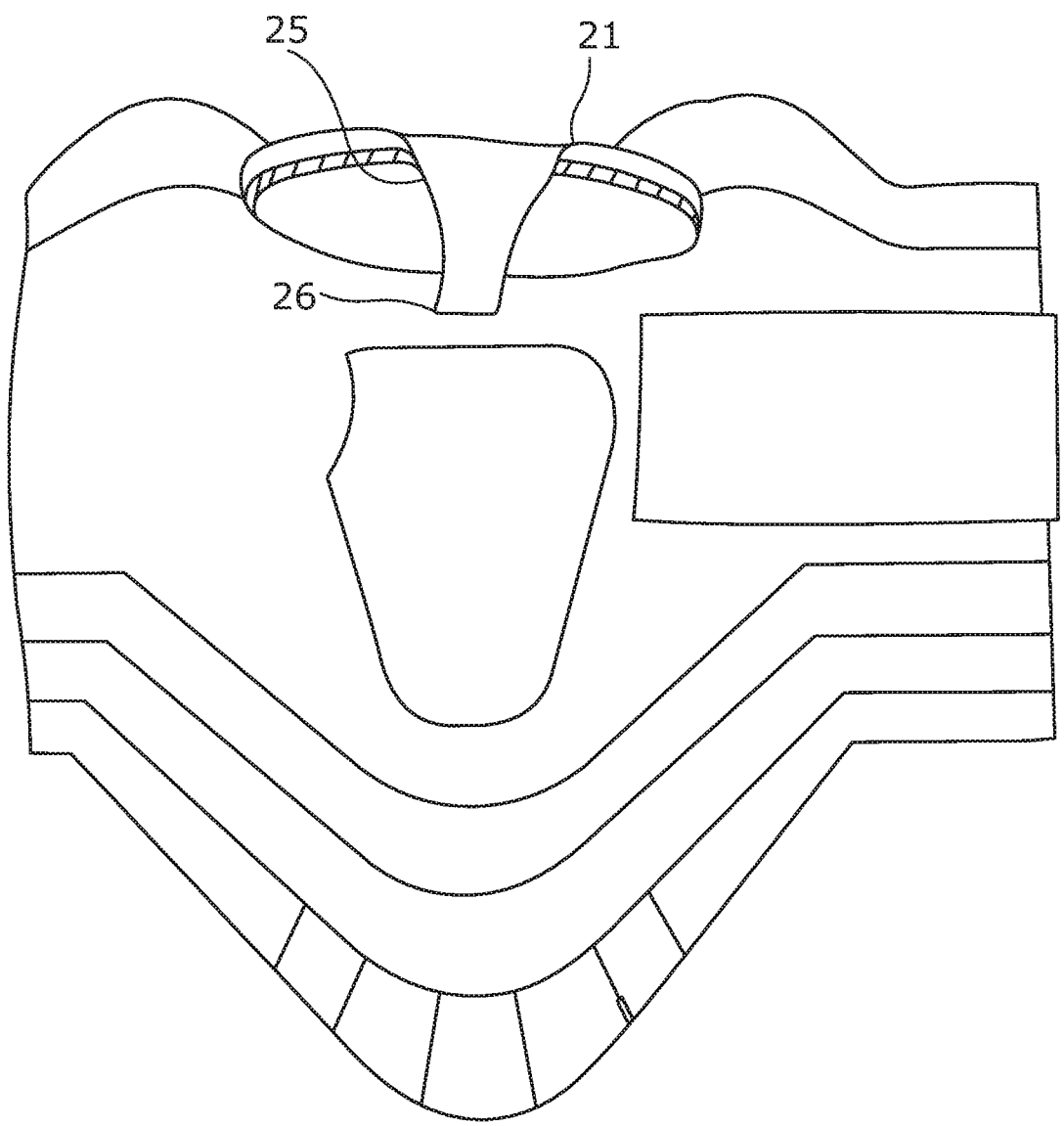
FIG. 3 shows a front plan view of the neck brace with the chin support attached.

In FIG. 3, the chin support of the neck brace is illustrated, in this embodiment the chin support 21 is shown as a separate attachment in the form of an elliptical member that is attached to the main body of the brace, front section 18, toward upper side 11 using a strap 25 that fits through a slit 26 in the brace and is fastened to the opposite side of front section 18 in conventional fashion. Although not shown, chin support 21 may be an integral part of section 18 and represents an extended part of upper side 11 that is simply folded down when in use.

In use, an emergency kit comprises at least one neck brace. Due to the light weight of the materials the brace can be transported relatively easily to a site of use then once the brace is unfolded its size can be adjusted by folding the brace along one of the selected crease lines in order to reduce its size. In the instance where the crease lines are perforated, a user can tear the brace along a selected crease line in order to provide a brace of an appropriate size.

The invention thus elegantly deals with a need to provide emergency support in times of crisis for a number of people whose requirements differ.

The invention claimed is:

1. A neck brace, comprising:
    a blank having an axis of symmetry along a mid-line and a front and rear section extending symmetrically from either side of said mid-line, each of said front and rear section comprising:
    i) a lower edge, an upper edge, an inner side edge and an outer side edge wherein said lower edge is fashioned to provide a single wave formation and said upper edge is fashioned to provide at least two wave formations, further wherein an axis of symmetry of said single wave formation is aligned with an axis of symmetry of said at least two wave formations;

ii) at least one crease line that mirrors a contour of at least said lower edge single wave formation, the at least one crease line being spaced from at least said lower edge by a selected amount whereby at least said lower edge can be folded or torn along said at least one crease line to size the blank to fit a user;

iii) at least one fastening member attached to or associated with said front and rear section, near or at said front and rear side outer edges; and a chin supporting member attached to or associated with said upper edge of said front section.

2. The neck brace according to claim 1 wherein said chin supporting member is positioned between adjacent wave formations of said at least two wave formations of said upper edge.

3. The neck brace according to claim 1 wherein said chin supporting member comprises a portion of said blank which is hingedly attached to said front section for pivoting into position.

4. The neck brace according to claim 1 wherein said chin supporting member comprises a portion of said blank which is releasably attached to said front section whereby, in use when attached, said chin supporting member projects forward from said front section.

5. The neck brace according to claim 1 wherein at or between said side inner edges of said front and rear sections is provided at least one adjustment member whereby the said inner edges of said front and rear sections can be brought together by a selected amount.

6. The neck brace according to claim 5 wherein said adjustment member comprises a strap and associated restraining member.

7. The neck brace according to claim 1 wherein said blank is formed from a stiff but flexible material.

8. The neck brace according to claim 7 wherein said material is cardboard.

9. The neck brace according to claim 1 wherein said blank is a corrugated material.

10. The neck brace according to claim 1 wherein said blank is formed from at least two materials comprising: a first stiff but flexible material and a second flexible material.

11. The neck brace according to claim 10 wherein said materials are overlain.

12. The neck brace according to claim 10 wherein said first stiff but flexible material is cut in the same shape as said second flexible material but is smaller whereby, when overlain, the said second flexible material provides a margin about said first flexible material.

13. The neck brace according to claim 10 wherein at least said lower edge is provided with at least one cut or tear.

14. The neck brace according to claim 13 wherein at least said lower edge is provided with a plurality of cuts or tears extending inwards from said edge.

15. The neck brace according to claim 14 wherein said plurality of cuts or tears are at right angles with respect to said lower edge.

16. The neck brace according to claim 13 wherein said at least one cut or tear is provided in the region of a peak of said single wave formation of said lower edge.

17. The brace according to claim 13 wherein said at least one cut or tear is provided in the said second flexible material.

18. The neck brace according to claim 1 wherein said at least one crease line also mirrors a contour of said at least one side edge but is spaced therefrom by a selected amount.

19. The neck brace according to claim 1 wherein said at least one crease line also mirrors a contour of said front and rear inner and/or outer side edges but is spaced therefrom by a selected amount.

20. The neck brace according to claim 1 wherein said at least one crease line also mirrors a contour of said upper edge but is spaced therefrom by a selected amount.

21. The neck brace according to claim 1 wherein three of said crease lines are provided and they are designated, proceeding inwardly from the lower or upper edge and/or side edge(s), as large medium, and small.

22. The neck brace according to claim 1 wherein said at least one crease line is also perforated whereby the outer part(s) can be torn away from the main body of the brace.

23. The neck brace according to claim 1 wherein said front section has an opening located in said brace so that, in use, it is aligned with a throat of a user.

24. The neck brace according to claim 1 wherein said fastening member comprises complementary mating members.

25. The neck brace according to claim 24 wherein said fastening member comprises a member selected from the group comprising: VELCRO® hook and loop material, clasp members, hook/eye members, stud/socket members, magnetic members and adhesive members.

26. The neck brace according to claim 1 wherein said brace is disposable.

* * * * *